US00PP30100P2

(12) United States Plant Patent
Pavlich

(10) Patent No.: US PP30,100 P2
(45) Date of Patent: Jan. 15, 2019

(54) ***BEGONIA* PLANT NAMED 'TNBEGSS'**

(50) Latin Name: ***Begonia* spp.**
Varietal Denomination: TNBEGSS

(71) Applicant: Terra Nova Nurseries, Inc., Canby, OR (US)

(72) Inventor: John C. Pavlich, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/732,552

(22) Filed: Nov. 27, 2017

(51) Int. Cl.
*A01H 5/02* (2018.01)

(52) U.S. Cl.
USPC ..... Plt./257

(58) Field of Classification Search
USPC ..... Plt./343
See application file for complete search history.

*Primary Examiner* — Susan McCormick Ewoldt
(74) *Attorney, Agent, or Firm* — Klarquist Sparkman, LLP

(57) ABSTRACT

A new and distinct form of *Begonia* plant characterized by broad, maple-shaped leaves of glowing silver-white with mint green in a starry pattern along the veins, bright red-pink sterile flowers, an upright, bushy habit (perfect as a container plant), a vigorous and well-branched bushy habit, and excellent vigor.

1 Drawing Sheet

Botanical denomination: *Begonia* spp.
Variety designation: 'TNBEGSS'.

BACKGROUND

The present invention relates to a new and distinct cultivar of *Begonia*, of the family Begoniaceae, and given the cultivar name, 'TNBEGSS'. The new cultivar was developed in a planned breeding program to produce unique container plants with showy flowers. The new cultivar originated from cross between *Begonia taliensis*, an unpatented plant, as the seed parent, and *Begonia taliensis* 12-0121, a proprietary, unreleased seedling, as the pollen parent.

Compared to the seed parent, *Begonia taliensis*, the new cultivar has smaller, more silver leaves on shorter petioles and has an upright branching habit rather than a rosette habit.

Compared to the pollen parent, *Begonia taliensis* 12-0121, the new cultivar has a larger habit with more palmate leaves that are more heavily silvered.

Compared to *Begonia* HOLIDAY™ 'Snowflake' (unpatented),the new cultivar is more spreading, better branched, and has larger female flowers that are retained for a longer period of time.

This selection is uniquely characterized by:

1. broad, maple-shaped leaves of glowing silver-white with mint green in a starry pattern along the veins,
2. bright red-pink sterile flowers,
3. an upright, bushy habit, perfect as a container plant,
4. a vigorous and well-branched bushy habit, and
5. excellent vigor.

The new variety has been reproduced only by asexual propagation (leaf cuttings and tissue culture using apical tips). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of a leaf of *Begonia* 'TNBEGSS'.

FIG. 2 shows a one and a half year old plant of the new cultivar grown in a warm greenhouse in Canby, Oreg.

DETAILED PLANT DESCRIPTION

The following is a detailed description of the new *Begonia* cultivar based on observations of one-year-old specimens grown in 5" hanging basket in a warm greenhouse in November in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart, 5th* edition, 2007.

Plant:

*Type*.—Herbaceous rhizomatous perennial.
*Form*.—Clumping, caulescent.
*Cold hardiness*.—USDA Zone 10a.
*Size*.—Grows to 34 cm tall and 70 cm wide.
*Vigor*.—Excellent.
*Roots and rooting*.—Roots appear on leaf cuttings in 2 weeks; fine, fibrous, and white in color, White NN155A.

Stem:

*Type*.—Upright, branching.
*Size*.—Grows to 35 cm long and 10 mm wide.
*# stems from base*.—20.
*Lateral branches*.—1 to 2 per stem.
*Internodes*.—About 3 cm to 11 cm long.
*Stem strength*.—Good.
*Surface*.—Sparsely pubescent.
*Color*.—Greyed Purple 187A.

Leaf:

*Type*.—Simple.

*Arrangement*.—Alternate.

*Number*.—About 100.

*Shape*.—Obliquely broadly ovate to orbicular with 6 to 9 shallow palmate lobes.

*Margins*.—Coarsely serrate.

*Apex*.—Acuminate.

*Base*.—Oblique, cordate.

*Venation*.—Palmate, Greyed Yellow 160D on topside, bottom side closest to Greyed Orange 177D.

*Blade size*.—Grows to 1.5 cm wide and 16 cm long.

*Surface texture*.—Pubescent both sides.

*Leaf strength*.—Good.

*Stipules*.—Deciduous, elliptical, grow to 12 mm long and 7 mm wide, apex mucronulate, base clasping, margin entire, topside glabrous, bottom side pubescent, both sides Greyed Orange 177D on the sides and Greyed Red 187D in the middle.

*Petiole description*.—Grows to 19 cm long and 5 mm wide, succulent, pubescent, Greyed Purple 187A.

*Leaf color*.—Top side — Greyed Green 190C over most of leaf, with Green 136A from the sinus and up the veins; bottom side closest to Greyed Green 195A tinted Red Purple 61A near veins.

Inflorescence:

*Type*.—Axillary, bisexual, cymose.

*Number of flowers per cyme*.—4 to 8.

*Peduncle description*.—Grows 8 cm long and 2.5 mm wide, glabrous, strong, Greyed Purple 187B, branching, branches weak; with 2 opposite, dehiscent petiolate leaf-bracts below each cyme, lanceolate, 6 mm wide and 10 mm long, margins entire, tip apiculate, topside pubescent, bottom side glabrous, both sides Yellow Green 160C with parallel veins of Red Purple 61B.

*Pedicel description*.—Weak in strength, grow to 5 mm long, 2 mm wide, fleshy, glabrous, Red Purple 61A.

*Bloom period*.—Year round in Canby, Oreg.

Flower bud:

*Size*.—Staminate flowers grow to 20 mm long and 12 mm wide; pistillate flowers are 20 mm deep and 13 mm wide prior to opening.

*Shape*.—Teardrop.

*Surface texture*.—Pubescent.

*Color*.—Red Purple 63A.

Flower:

*Type*.—Monoecious, bilaterally symmetrical, single.

*Pistillate flower*.—Grows to 30 mm deep and 37 mm wide overall, corolla doesn't fully open, grows to 20 mm deep and 10 mm wide; 2 fleshy tepals, fused near base for 6 mm, each grow to 19 mm long and 10 mm wide, obovate, tip and base obtuse, margins entire, glabrous inside and out, inside and outside Red Purple 63C blending to 63B near margins; pistil 1, 26 mm long and 37 mm wide, style 1 mm long and 3 mm wide, Greyed Yellow 161A, stigma 3-branched, twisted and papillose, over an area 7 mm wide and 6 mm deep, Greyed Yellow 161A, ovary to 37 mm wide and 20 mm deep, three-winged, two equal and one longer, Yellow Green 147B tints in ovary edges blending to Red Purple 63C.

*Staminate flower*.—Grow to 20 mm long and 12 mm wide, stays bud-like, unopened, Red Purple 63A.

*Fragrance*.—None.

*Lastingness*.—A cyme blooms for about 4 weeks on the plant, flowers are self-cleaning.

Fruit and seed: None, sterile.

Diseases and pests: No known resistances to pests or diseases. No problems have been found in Canby, Oreg.

I claim:

1. A new and distinct form of *Begonia* plant as hereby illustrated and described.

* * * * *

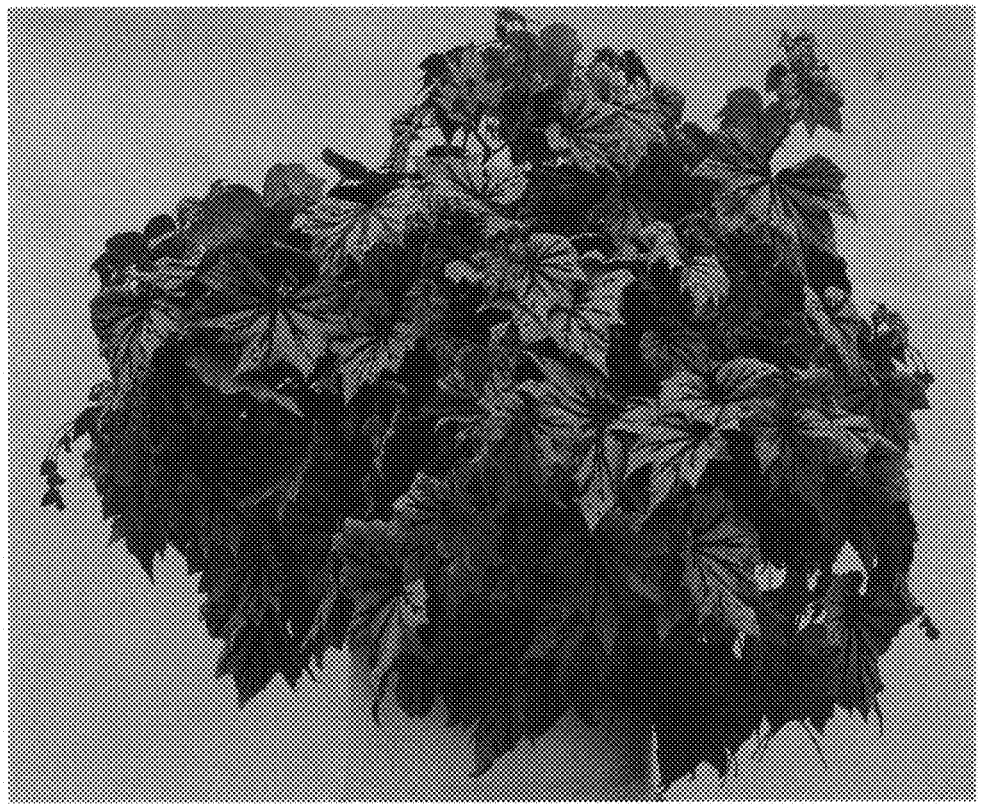

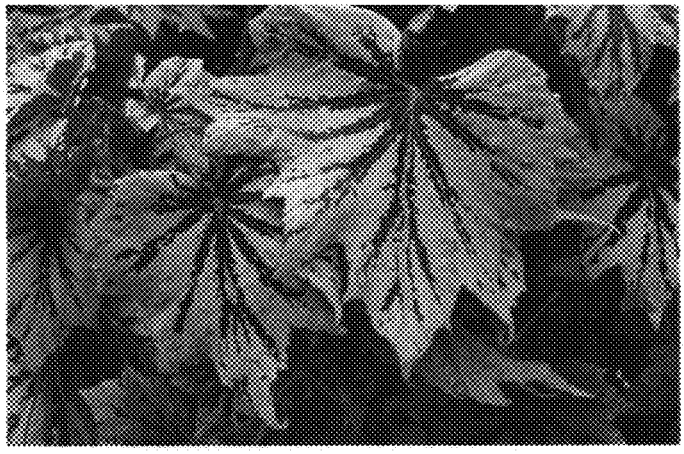
FIG. 1 on left,
FIG. 2 below